United States Patent [19]

Ikeda et al.

[11] Patent Number: 5,362,423

[45] Date of Patent: Nov. 8, 1994

[54] METHOD OF PRODUCING PENTAFLUOROPHENYLMAGNESIUM DERIVATIVES USING PENTAFLUOROBENZENE

[75] Inventors: Yoshihiko Ikeda, Shinnanyo; Takeo Yamane, Ogori; Eiichi Kaji; Kenji Ishimaru, both of Shinnanyo, all of Japan

[73] Assignee: Tosoh Akzo Corporation, Tokyo, Japan

[21] Appl. No.: 169,074

[22] Filed: Dec. 20, 1993

[30] Foreign Application Priority Data

Dec. 28, 1992 [JP] Japan .................................. 4-361482

[51] Int. Cl.$^5$ ................................................ C07F 3/02
[52] U.S. Cl. ................................ 260/665 R; 260/665 G
[58] Field of Search ....................... 260/665 R, 665 G

[56] References Cited

U.S. PATENT DOCUMENTS 3,700,693 10/1972 Cairncross et al. ............. 260/665 X Primary Examiner—Paul F. Shaver
Attorney, Agent, or Firm—Oblon, Spivak, McClelland, Maier & Neustadt

[57] ABSTRACT

Disclosed is a production method, wherein, with pentafluorobenzene represented by $C_6HF_5$, 0.5 to 1.5 equivalents of organometallic compound represented by a general formula $$R_{2-n}MgX_n$$

(wherein n denotes a real number of 0 or 1, X denotes a halogen atom, R denotes a hydrocarbon group with carbon atoms of 1 to 10, and said hydrocarbon group may contain functional groups unaffecting the reaction) are mixed within a temperature range from −40° to 250° C. in an ether type solvent or a mixed nonaqueous solvent of ether type solvent with hydrocarbon type solvent and reacted at 25° C. or higher to obtain pentafluorophenylmagnesium derivatives represented by a following general formula $$(C_6F_5)_{2-n}MgX_n$$

(wherein n denotes a real number of 0 or 1 and X denotes a halogen atom).

1 Claim, No Drawings

METHOD OF PRODUCING PENTAFLUOROPHENYLMAGNESIUM DERIVATIVES USING PENTAFLUOROBENZENE

BACKGROUND OF THE INVENTION

The present invention relates to a method of efficiently and economically producing pentafluorophenylmagnesium derivatives using pentafluorobenzene as a raw material. The pentafluorophenylmagnesium derivatives are very useful raw materials for pentafluorophenylation and used as important reactants when producing various intermediates for medicinal drugs or boron derivatives which are very useful as cocatalysts for cationic complex polymerization, for example, tris(pentafluorophenyl)borane and tetrakis(pentafluorophenyl)borate derivatives by reacting them with boron compounds such as boron trifluoride or boron trichloride.

In the conventional production method of pentafluorophenylmagnesium derivatives, very expensive pentafluorobromobenzene is generally used as a starting material for the source of pentafluorophenyl group. For example, there are J. Chem. Soc., 166 (1959), Z. Naturforschg., 20b, 5 (1965), Synthesis of Fluoroorganic Compounds, p. 141, Springer-Verlag (1985), etc. Moreover, in the production method using pentafluorobenzene as a starting material for the source of pentafluorophenyl group when producing pentafluorophenylmagnesium derivatives, it is reported that pentafluorophenylmagnesium derivatives can be obtained in a yield of 86% by using tetrahydrofuran as a reaction solvent and reacting for 5 hours at room temperature (J. Org. Chem., 29, 2385 (1964)).

In the conventional production method using pentafluorobenzene as a starting material for the source of pentafluorophenyl group, tetrahydrofuran is used as a reaction solvent. However, in a reaction system such that strong Lewis acids such as titanium tetrachloride, boron trichloride, boron trifluoride and tin tetrachloride coexist, tetrahydrofuran ends up to polymerize, hence a production method in other reaction solvent system difficult in polymerization has been required. Moreover, while pentafluorobromobenzene being a starting material for the source of pentafluorophenyl group is very expensive, pentafluorobenzene is also relatively expensive, hence, the improved yield has been desired also in the production method using pentafluorobenzene as a starting material and tetrahydrofuran as a reaction sovlent.

In view of said situation, the inventors investigated extensively on a process which has a versatility as a production method of pentafluorophenylmagnesium derivatives using pentafluorobenzene as a starting material, in which the yield is quantitative and the application scope is broad, and which is more economical not requiring a temperature as very low as −70° C. on production over pentafluorophenyllithium used for the similar reaction, leading to the invention.

SUMMARY OF THE INVENTION

The invention relates to a production method wherein, with pentafluorobenzene represented by a following formula [I], $$C_6HF_5 \qquad [I]$$

0.5 to 1.5 equivalents of organometallic compound represented by a general formula [II]

$$R_{2-n}MgX_n \qquad [II]$$

(wherein n denotes a real number of 0 or 1, X denotes a halogen atom, R denotes a hydrocarbon group with carbon atoms of 1 to 10, and said hydrocarbon group may contain functional groups unaffecting the reaction) are mixed within a temperature range from −40° to 250° C. in an ether type solvent or a mixed nonaqueous solvent of an ether type solvent with a hydrocarbon type solvent and reacted at 25° C. or higher to obtain pentafluorophenylmagnesium derivatives represented by a following general formula [III]

$$(C_6F_5)_{2-n}MgX_n \qquad [III]$$

(wherein n denotes a real number of 0 or 1 and X denotes a halogen atom).

DETAILED DESCRIPTION OF THE INVENTION

In following, the invention will be illustrated in detail.

The ether type solvents referred to so in the invention indicate diethyl ether, dipropyl ether, diisopropyl ether, dibutyl ether, diisoamyl ether, 1,2-dimethoxyethane, 1,2-diethoxyethane, di-2-methoxyethyl ether, tetrahydrofuran, tetrahydropyran, 1,4-dioxane, etc. From the easiness in the progression of deprotonation reaction of pentafluorobenzene, tetrahydrofuran, tetrahydropyran, 1,4-dioxane, 1,2-dimethoxyethane, 1,2-diethoxyethane or di-2-methoxyethyl ether is desirable.

Next, the hydrocarbon type solvents referred to so in this specification indicate saturated hydrocarbons such as pentane, isopentane, hexane, cyclohexane, heptane, octane, nonane, decane, undecane, dodecane, tridecane, tetradecane, pentadecane, hexadecane, n-paraffin and petroleum ether, aromatic hydrocarbons such as benzene, toluene, o-xylene, m-xylene, p-xylene, 1,2,3-trimethylbenzene, 1,2,4-trimethylbenzene, 1,2,5-trimethylbenzene, 1,3,5-trimethylbenzene, ethylbenzene, propylbenzene and butylbenzene, and mixtures of these.

Next, the functional groups unaffecting the reaction in the formula [II] referred to so in this specification include methyl group, ethyl group, propyl group, isopropyl group, propenyl group, 2-isopropenyl group, allyl group, butyl group, sec-butyl group, tert-butyl group, isobutyl group, pentyl group, sec-pentyl group, tert-pentyl group, neo-pentyl group, sec-isopentyl group, hexyl group, sec-hexyl group, isohexyl group, sec-isohexyl group, cyclohexyl group, phenyl group, benzyl group, o-tolyl group, m-tolyl group, p-tolyl group, methoxymethyl group, methylthiomethyl group, 2-dimethylaminoethyl group, o-anisyl group, m-anisyl group, p-anisyl group, trimethylsilylmethyl group, etc.

Next, exemplifying some of organomagnesium compounds represented by the formula [II] referred to so in the invention, there are methylmagnesium iodide, methylmagnesium bromide, methylmagnesium chloride, dimethylmagnesium, ethylmagnesium bromide, ethylmagnesium chloride, ethylmagnesium iodide, diethylmagnesium, propylmagnesium bromide, propylmagnesium chloride, butylmagnesium bromide, butylmagnesium chloride, sec-butylmagnesium bromide, sec-butylmagnesium chloride, tert-butylmagnesium bromide, tert-butylmagnesium chloride, isobutylmagnesium bromide, isobutylmagnesium chloride, hexylmagnesium bromide, hexylmagnesium chloride, cyclohexylmagnesium bromide, cyclohexylmagnesium chloride, ethylbutylmagnesium, dibutylmagnesium, etc.

The concrete method for production will be described below in sequence. The method of generating pentafluorophenylmagnesium derivatives represented by the formula [III] includes following method. Pentafluorobenzene represened by the formula [I] is dissolved into an ether type solvent, a hydrocarbon type solvent or a mixed solvent thereof. With this solution, 0.5 to 1.5 equivalents of organomagnesium compound represented by the formula [II] are mixed within a range from $-40°$ to $250°$ C.

In this reaction, because of relatively low reactivity of organomagnesium compound represented by the formula [II], if it is used in excess to pentafluorobenzene represented by the formula [I], then a large quantity of unreacted organomagnesium compound represented by the formula [II] remains to produce the impurities in large quantities, hence it is desirable to use 0.8 to 1.2 equivalents of organomagnesium compound represented by the formula [II]. If the reaction temperature is lower than $25°$ C., then the progress of reaction becomes very slow and, if it is too high beyond $200°$ C., then the progress of side reaction becomes very fast, resulting in a very low yield in both cases, hence mixing within a range from $25°$ C. to $200°$ C. is desirable. The reaction mixture is reacted for 0.5 hours or longer at $25°$ C. or higher, desirably for 0.5 hours or longer at $40°$ C. or higher to prepare pentafluorophenylmagnesium derivatives represented by the formula [III].

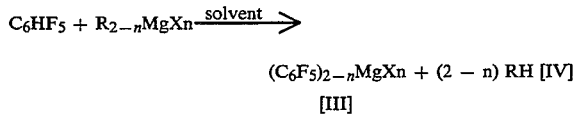

$$(C_6F_5)_{2-n}MgX_n + (2 - n) RH \quad [IV]$$
$$[III]$$

(wherein n denotes a real number of 0 or 1, X denotes a halogen atom, R denotes a hydrocarbon group with carbon atoms of 1 to 10, and said hydrocarbon group may contain functional groups unaffecting the reaction).

In the investigations of the invention, the reaction solvent, reaction temperature, time and composition of organomagnesium compound [II] were varied for obtaining [III] stably in high yield after the progression of equation [IV].

Explaining the equation [IV] in detail, with pentafluorobenzene represented by the formula $C_6HF_5$ [I], 0.5 to 1.5 equivalents of organometallic compound represented by the general formula [II]

$$R_{2-n}MgX_n \quad [II]$$

(wherein n denotes a real number of 0 or 1, X denotes a halogen atom, R denotes a hydrocarbon group with carbon atoms of 1 to 10, and said hydrocarbon group may contain functional groups unaffecting the reaction) are mixed within a temperature range from $-40°$ to $250°$ C. in an ether type solvent or a mixed nonaqueous solvent of ether type solvent with a hydrocarbon type solvent and reacted at $25°$ C. or higher, thereby allowing pentafluorophenylmagnesium derivatives represented by the following general formula [III]

$$(C_6F_5)_{2-n}MgX_n \quad [III]$$

(wherein n denotes a real number of 0 or 1 and X denotes a halogen atom) to generate quantitatively and stably.

Moreover, similar effect has been achieved also by replacing with a chain ether type reaction solvent resistant to strong Lewis acids. Furthermore, even by replacing with a chain ether type reaction solvent resistant to strong Lewis acids, the synthesis of pentafluorophenylmagnesium derivatives has become possible.

Still more, the reaction yield of pentafluorophenylmagnesium derivatives has become possible to be enhanced by pursuing the reactivity in respective reaction solvents through the reaction with carbon dioxide or the measurement of $^{19}F$-NMR or the effects of R and $X_n$ in $R_{2-n}MgX_n$ represented by the general formula [II] have also become possible to be known by pursuing the reaction, leading to the invention. The reaction yield was determined from the production rate of pentafluorobenzoic acid and the ratio of $F^{a)}$ at ortho position.

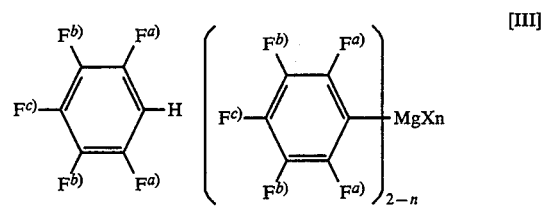

(wherein n denotes a real number of 0 or 1).

The invention can provide a method of producing pentafluorophenylmagnesium derivatives in a higher yield and at lower cost over the conventional method by replacing very expensive pentafluorobromobenzene with pentafluorobenzene as a starting material for the source of pentafluorophenyl group.

Moreover, in comparison with the conventional production method using pentafluorobenzene as a starting material for the source of pentafluorophenyl group, it has become possible to obtain pentafluorophenylmagnesium derivatives in a higher yield even in the case of using tetrahydrofuran as a reaction solvent. In addition, similar effect has been achieved also by replacing with a chain ether type reaction solvent resistant to Lewis acids, making it possible to synthesize pentafluorophenylmagnesium derivatives in a quantitative yield.

In following, the invention will be illustrated in more detail using the examples, but the invention is subject to no restriction by the following examples so long as the gist is not exceeded.

EXAMPLE 1 AND 3 (TABLE 1)

Into a 200 ml volume three-neck flask sufficiently replaced with nitrogen, a 18.5 wt. % tetrahydrofuran solution of 50.15 g (69.6 mmol) of ethylmagnesium bromide was charged. A mixed solution of 12.86 g (76.5 mmol) of pentafluorobenzene with 30 ml of tetrahydrofuran was added dropwise thereinto from a dropping funnel. The temperature at that time was $25°$ to $30°$ C. After the completion of dropwise addition, aging was performed for 2 hours and 15 hours at $40°$ C. Taking each 0.3 ml from that reaction solution, the aliquots were mixed with 0.3 ml of deuterated benzene under an atmosphere of nitrogen to make sample solutions for the $^{19}F$-NMR measurement. As a result of the determination of the reaction yield by said method, they showed to be 99.8 to 100% in both cases.

Comparative Example 1 (Table 1)

Into a 200 ml volume three-neck flask sufficiently replaced with nitrogen, a 18.5 wt. % tetrahydrofuran solution of 50.00 g (69.4 mmol) of ethylmagnesium bromide was charged. A mixed solution of 12.85 g (76.5 mmol) of pentafluorobenzene with 30 ml of tetrahydrofuran was added dropwise thereinto from a dropping funnel. The temperature at that time was 15° to 20° C. After the completion of dropwise addition, aging was performed for 5 hours at 20° C. Taking 0.3 ml from that reaction solution, the aliquot was mixed with 0.3 ml of deuterated benzene under an atmosphere of nitrogen to make a sample solution for the $^{19}$F-NMR measurement. As a result of the determination of the reaction yield by said method, it showed to be 87.9%.

Other results are shown in Table 1 below.

characterized in that with pentafluorobenzene represented by a following formula [I], $$C_6HF_5 \quad [I]$$

0.5 to 1.5 equivalents of organometallic compound represented by a general formula [II]

$$R_{2-n}MgX_n \quad [II]$$

wherein n denotes a real number of 0 or 1, X denotes a halogen atom, R denotes a hydrocarbon group with carbon atoms of 1 to 10, and said hydrocarbon group may contain functional groups unaffecting the reaction are mixed within a temperature range from −40° to 250° C. in an ether type solvent or a mixed nonaqueous solvent of an ether type solvent with a hydrocarbon type solvent and reacted at 25° C. or higher to obtain pentafluorophenylmagnesium derivatives represented

TABLE 1

| No. | Grignard's reactant | Reaction solvent | Reaction conditions Temperature | Time | Yield (%) |
|---|---|---|---|---|---|
| Example 1 | EtMgBr | Tetrahydrofuran | 40° C. | 2 hr | 100 |
| Example 2 | EtMgCl | Tetrahydrofuran | 40° C. | 15 hr | 100 |
| Example 3 | EtMgBr | Tetrahydrofuran | 40° C. | 15 hr | 100 |
| Example 4 | EtMgBr | 1,2-Dimethoxyethane | 25° C. | 2 hr | 100 |
| Example 5 | PrMgCl | 1,2-Dimethoxyethane | 25° C. | 2 hr | 100 |
| Example 6 | PrMgCl | 1,2-Dimethoxyethane | 40 1C | 2 hr | 100 |
| Example 7 | BuMgCl | Tetrahydrofuran | 40° C. | 15 hr | 100 |
| Example 8 | sec-BuMgCl | 1,2-Dimethoxyethane | 25° C. | 2 hr | 100 |
| Example 9 | cyclo-$C_4H_{11}$MgCl | 1,2-Dimethoxyethane | 25° C. | 2 hr | 100 |
| Example 10 | EtBuMg | 1,2-Dimethoxyethane | 40° C. | 15 hr | 100 |
| Comparative example 1 | EtMgBr | Tetrahydrofuran | 20° C. | 5 hr | 87.9 |
| Comparative example 2 | EtMgBr | Ethyl ether | 20° C. | 2 hr | 0 |
| Comparative example 3 | MeMgBr | Tetrahydrofuran | 0° C. | 15 hr | 0 | by a following general formula [III]

$$(C_6F_5)_{2-5}MgX_n \quad [III]$$

What is claimed is:

1. A method for producing pentafluorophenylmagnesium derivatives employing pentafluorobenzene wherein n denotes a real number of 0 or 1 and X denotes a halogen atom.

* * * * *